(12) United States Patent
Fulkerson et al.

(10) Patent No.: US 6,344,044 B1
(45) Date of Patent: Feb. 5, 2002

(54) APPARATUS AND METHODS FOR DELIVERY OF INTRALUMINAL PROSTHESIS

(75) Inventors: John Fulkerson; Rogelio Pepa; Isa Rizk; Karim Mouneimne, all of Laguna Hills, CA (US)

(73) Assignee: Edwards Lifesciences Corp.

( * ) Notice: Subject to any disclaimer, the term of this patent is extended or adjusted under 35 U.S.C. 154(b) by 0 days.

(21) Appl. No.: 09/503,618

(22) Filed: Feb. 11, 2000

(51) Int. Cl.[7] ............................................... A61M 29/00
(52) U.S. Cl. ..................................................... 606/108
(58) Field of Search ............................... 606/108, 191, 606/192, 195, 198, 200; 128/898; 623/1.11, 1.12

(56) References Cited

U.S. PATENT DOCUMENTS 5,261,916 A * 11/1993 Engelson .................... 606/191
5,800,455 A * 9/1998 Palermo et al. ............. 606/108
6,093,194 A * 7/2000 Mikus et al. ................ 606/108

* cited by examiner

*Primary Examiner*—Kevin Truong
(74) *Attorney, Agent, or Firm*—Vascular Systems Division; Peter Jon Gluck; Bruce M. Canter

(57) ABSTRACT

An apparatus and method for intraluminal delivery and deployment of an expandable prosthesis at a site within a body canal is provided. The apparatus comprises an elongated sleeve and an outer shaft disposed within the elongated sleeve and movable relative to the sleeve. A securing member is disposed on a distal area of the outer shaft. The expandable prosthesis is housed within a distal area of the elongated sleeve, and a distal area of the prosthesis is secured to the outer shaft by the securing member. The stent is deployed by displacing the sleeve in a proximal direction relative to the outer shaft to expose the stent and by releasing the stent from the securing member. If necessary, the stent can be repositioned prior to releasing the stent from the securing member.

4 Claims, 15 Drawing Sheets

US 6,344,044 B1

APPARATUS AND METHODS FOR DELIVERY OF INTRALUMINAL PROSTHESIS

FIELD OF THE INVENTION

The invention relates generally to an apparatus and method for delivering and deploying an expandable prosthesis within a body canal.

BACKGROUND OF THE INVENTION

Prostheses for transluminal implantation in body canals, such as blood vessels, for repair or dilation are known in the art. These prostheses may be tubular elements which are non-extendible or extendible (i.e. adapted to extend longitudinally), or they may be self-expanding in the transverse direction or expandable in the transverse direction by a dilation balloon. A typical self-expanding stent is disclosed in U.S. Pat. No. 4,655,771 to Wallsten. The stent has a radially and axially flexible, elastic tubular body with a predetermined diameter that is variable under axial movement of the ends and which comprises a plurality of individually rigid but flexible and elastic wire elements defining a radially self-expanding helix. This type of stent is known in the art as a "braided stent."

Another stent, which has particular applicability to the present invention is disclosed in U.S. Pat. No. 5,545,211 An et al. This stent has a greater tendency to resist foreshortening. It also has a significantly improved hoop strength which it is believed provides more radial force for maintaining the patency of a vessel lumen. As a consequence, this stent tends to resist compression.

A typical stent delivery device comprises a catheter assembly having a tubular sleeve with a self-expandable stent placed in contracted condition within a distal area of the sleeve. The sleeve is positioned by means of a guide wire and an introducer. The device further includes a means to expose the stent by sliding the sleeve away from the stent. The device can be directed to the site of implantation where the stent is released from the sleeve and implanted into the body canal.

One of the problems related to the placement of self-expanding prostheses such as stents is that they are highly compressed within delivery catheters to permit them to be maneuvered within the vascular system. The compressive forces necessary to reduce the stent have been found to lead to excessive friction between the stent and sleeve during deployment from the delivery catheters. Excessive friction may be particularly noticeable for stents which provide relative large radial forces for maintaining the patency of a body canal, such as the stent disclosed in U.S. Pat. No. 5,545,211. In addition, visualization of a compressed stent within the catheter is problematic, particularly when the stent must be placed near a branching body canal. Currently, hand held devices with pivoting levers have been utilized to provide the necessary forces to deploy the stent. Deployment of the stent at the desired location sometimes involves the process of partially deploying the stent and determining whether the stent is properly located in the vessel. The deployed portion of the stent may expand and impinge against the internal wall of the body canal. If the stent is improperly positioned, the stent may have to be recompressed and recaptured within the sleeve before moving it to a new location because friction between the stent and body canal would otherwise prevent movement of the prosthesis and/or because the body canal may be damaged by sliding the stent against the internal wall of the body canal. In some cases, it may not be possible to recompress and recapture the stent within the sleeve if the stent provide large radial forces for maintaining patency of a body canal.

Thus, there remains a need for a delivery device that is capable of partially deploying a stent and thereafter repositioning the partially deployed stent. There is also a need for repositioning a stent without having to recapture the stent within the sleeve. And, there is a need for partially deploying a stent having a high compressive force and repositioning such a stent.

SUMMARY OF THE INVENTION

In accordance with the present invention, a delivery and deployment apparatus is provided that is capable of partially deploying a stent and thereafter repositioning the stent without having to recapture the stent within a sleeve. The system of the present invention further permits the sleeve to be partially withdrawn and the delivery catheter to be repositioned without excessive frictional engagement with the body canal. The invention has particular applicability with a stent having a high compressive force, since the device of the present invention does not require recompression of the stent and recapture within the sleeve. Furthermore, the delivery apparatus actually utilizes the stent's compressive force to its advantage in that the repositioning of the stent relies on the column strength of the partially deployed stent to accurately reposition it.

In accordance with an illustrative embodiment of the present invention, the delivery apparatus comprises an elongated sleeve having a proximal end and a distal area with a distal end. A self-expandable prosthesis is placed in contracted condition within the distal area. An outer shaft is disposed within the sleeve and movable relative to the sleeve. A securing member is disposed on a distal area of the outer shaft, and a distal area of the prosthesis is secured to the outer shaft by the securing member. The delivery apparatus may further include an inner shaft which is disposed within the outer shaft and movable relative to the outer shaft. A tip is disposed at a distal end of the inner shaft and includes at least one side port for bleeding contrast medium adjacent to the atraumatic tip. The inner shaft may further include a lumen for receiving a guide wire.

The delivery apparatus may be operated in the following manner. The prosthesis is compressed and loaded into the distal area of the sleeve. The outer shaft is positioned within the prosthesis and sleeve, and the distal area of the prosthesis is secured to the securing member. Via the distal end of the outer shaft, the inner shaft is passed through the outer shaft until the atraumatic tips abuts against the securing member, thereby lockingly securing the prosthesis. With the prosthesis properly positioned within the body canal, the prosthesis is deployed by causing a longitudinal motion between the sleeve and outer shaft to expose the prosthesis and by releasing the securing member from the distal area of the prosthesis. If the prosthesis requires repositioning, retraction of the sleeve is terminated prior to releasing the prosthesis from the securing member. The prosthesis is then repositioned, the sleeve is fully retracted, and the prosthesis is released from the securing member.

Other objects, features, and advantages of the present invention will become apparent from a consideration of the following detailed description.

DETAILED DESCRIPTION OF THE PREFERRED EMBODIMENTS

Figure 1:
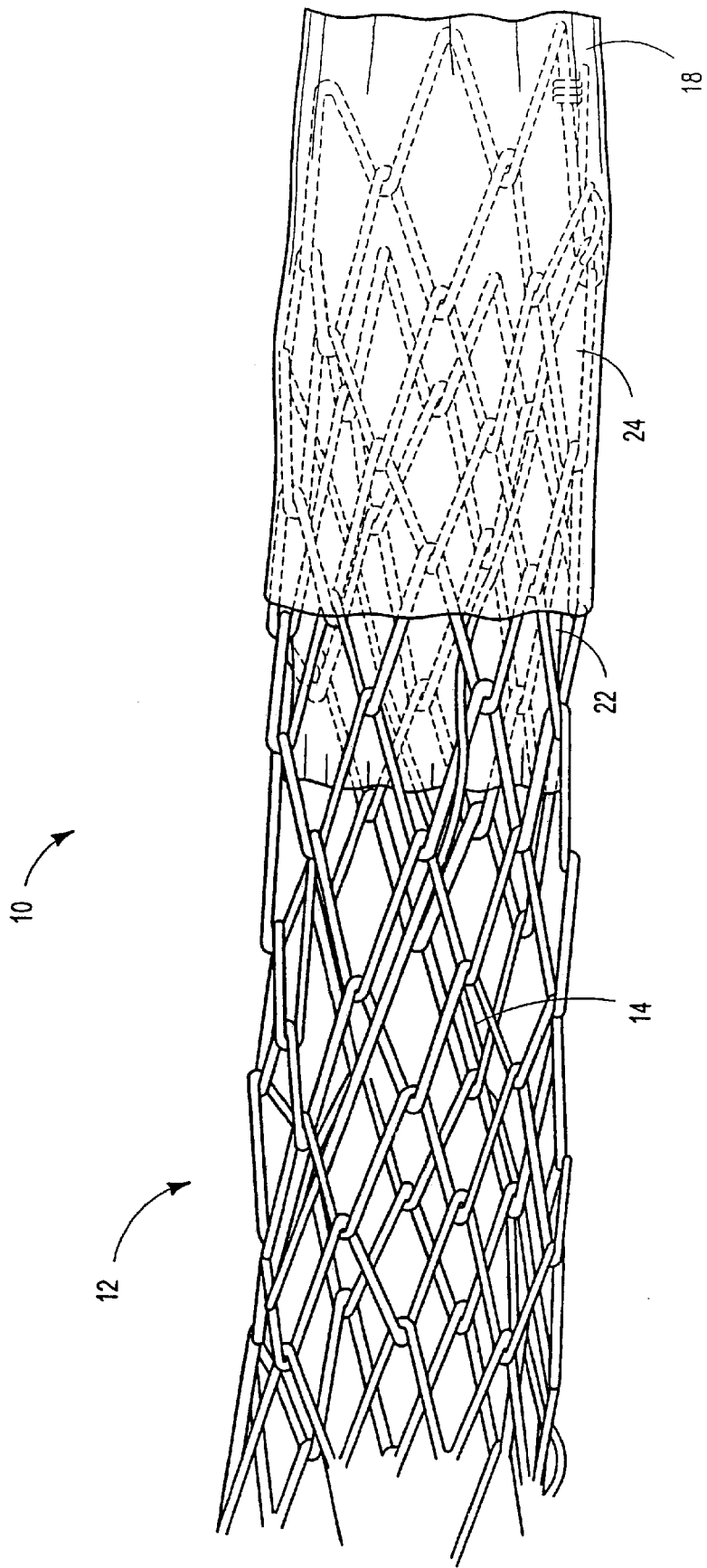
FIG. 1 is a side view of a vascular stent which is exemplary of the type of radially compressible tubular prosthesis which may be placed using a delivery apparatus in accordance with the present invention.

The present invention relates to a method and apparatus for intraluminal delivery and deployment of an expandable prosthesis at a site within a body canal. In the particular embodiment shown in the drawings and herein described, the apparatus is shown to deploy a self-expandable stent for a blood vessel. However, it should be understood that the principles of the invention are equally applicable to virtually any expandable prosthesis. For example, the apparatus may be used to deliver a self-expanding or balloon expandable graft, stent-graft or the like. Therefore, the present invention should not be limited to the specific embodiment shown and such principles should be broadly construed.

Referring to FIG. 1, an examplary prosthesis in the form of a self-expandable stent 10 is illustrated. The stent 10 comprises a wire frame 12 having a flexible tubular shape with rows of interconnected cells 14, and the ends of the frame 16, 18 include loops 20 extending longitudinally outward in the distal and proximal direction. The wire frame 12 is covered by an inner liner 22 and an outer liner 24, where the inner and outer liner encase or sandwich the frame. The liners 22, 24 may be joined together and affixed to the frame 12 by stitching, heat welding, ultrasonic welding or the like. In the exemplary embodiment, the liners 22, 24 are formed from polytetrafluoroethylene (PTFE) and are joined together by a process disclosed and claimed in commonly assigned U.S. Pat. No. 5,928,279, which is incorporated by reference as if fully described herein. It is contemplated that the length of the stent 10 may range from about 20 mm to 500 mm, preferably from 20 to 100 mm, and the relaxed diameter range from about 4 mm to 45 mm, preferably being in the range from about 5 mm to 25 mm. Such stents 10 are particularly suitable for the treatment of various occlusive conditions such as atherosclerotic or arteriosclerotic iliac artery stenosis and provides mechanical support to compress intimal flaps and dissections against the vessel wall after percutaneous tranluminal angioplasty. Additionally, the stent 10 mechanically supports arterial sclerotic plaque in the vessel passage, which inhibits restenosis and occlusion. The stent 10 may also be used for other applications such as to bridge an aneursym, or in a biliary, coronary, cerebral or any peripheral vascular site.

Figure 2:
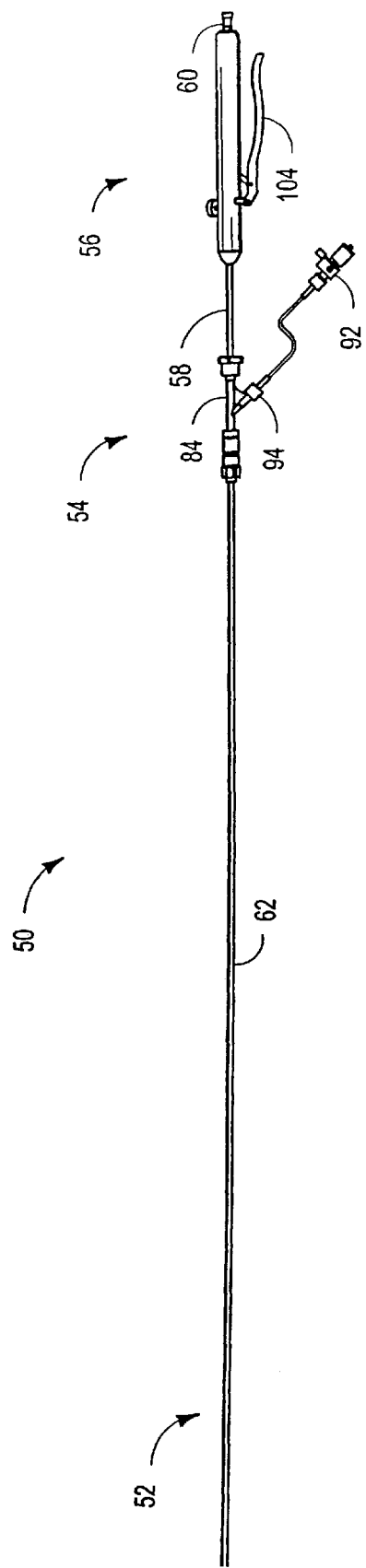
FIG. 2 is a side view of an examplary delivery apparatus in accordance with the present invention for delivering the stent shown in FIG. 1.

Referring to FIG. 2, a delivery and deployment apparatus 50 configured in accordance with the principles of the present invention is illustrated. It is noted that the delivery apparatus 50 may also be used to deliver non self-expanding prostheses such as a balloon expandable stent. The delivery apparatus 50 comprises a catheter assembly 52, a connector 54, and a hand piece 56. A proximal end of the connector 54 is coupled to the hand piece 56 by a tube 58, and the catheter assembly 52 extends outwardly from a proximal end of the connector 54.

Figure 3:
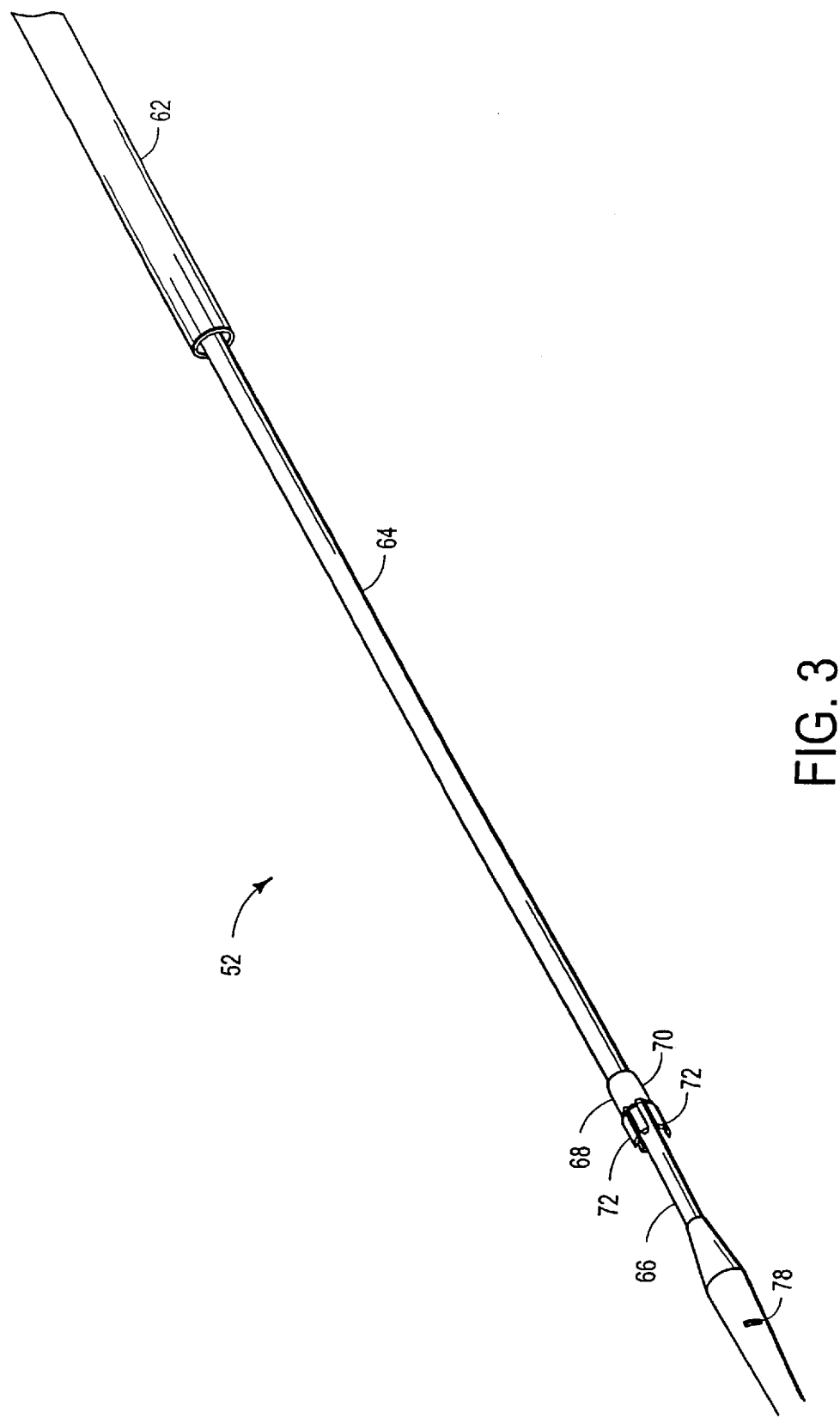
FIG. 3 is a close-up perspective view of the distal area of the delivery apparatus shown in FIG. 2.
Figure 4:
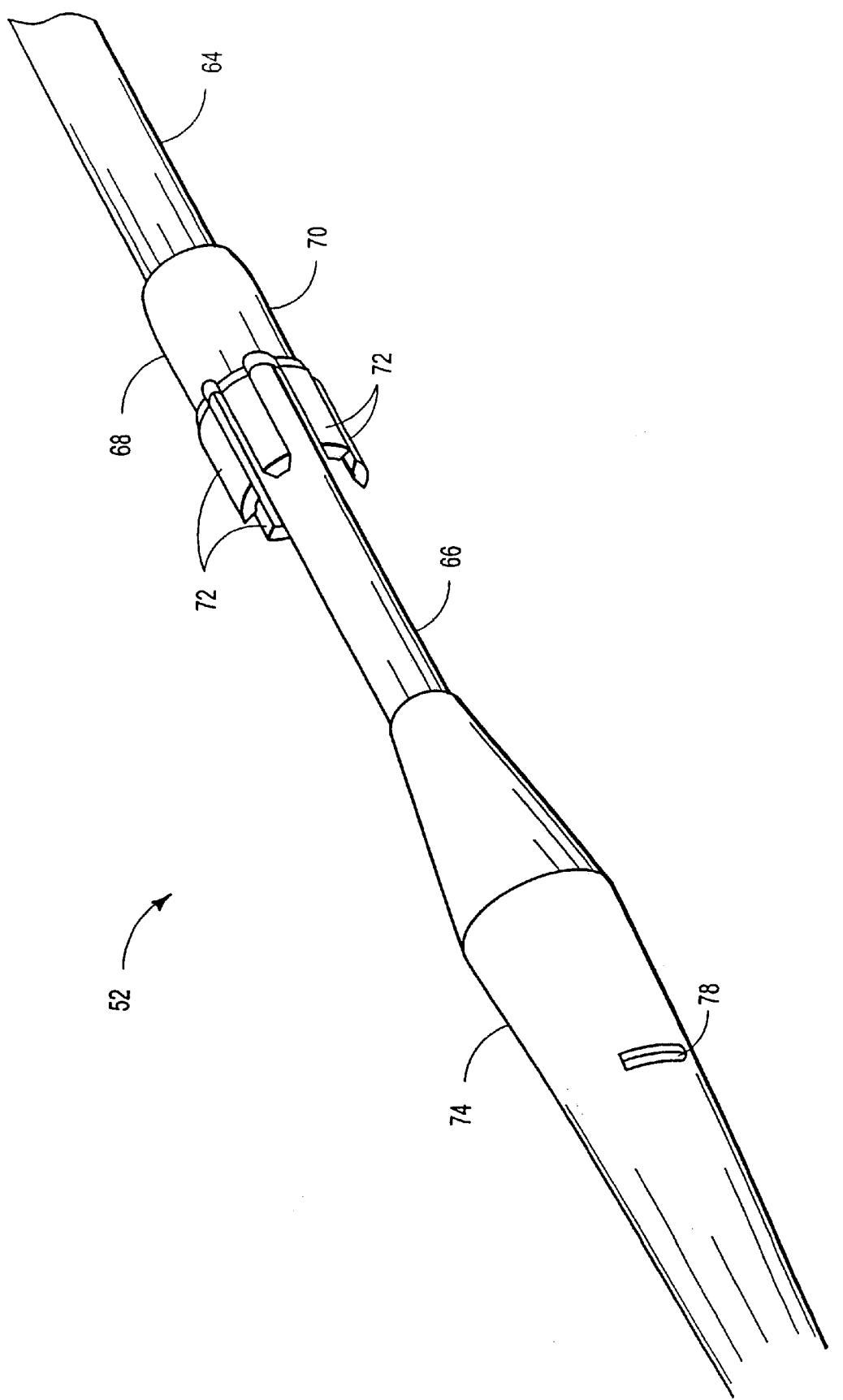
FIG. 4 is a further close-up perspective view of the distal area of delivery apparatus shown in FIG. 2.

Referring to FIGS. 3 and 4, the catheter assembly 52 is about 110 cm in length and includes a tubular sleeve 62, an outer shaft 64, and an inner shaft 66. The sleeve 62 has a lumen extending from a proximal end to a distal end, and the stent 10 (not shown) is housed within a distal area of the lumen in a compressed state. The outer shaft 64 is slidably received within the lumen and extends proximally beyond the proximal end of the sleeve 62. The outer shaft 64 has a lumen extending from a proximal end to a distal end, and the inner shaft 66 is slidably received within the lumen of the outer shaft 64. The proximal end of the inner shaft 66 extends proximally beyond the proximal end of the outer shaft 64 and is fixedly secured to the hand piece 56. The inner shaft 66 has a lumen for the passage of a guide wire (not shown) or other devices. A securing member 68 extends outwardly from the distal end of the outer shaft 64. In the examplary embodiment, the securing member 68 is shown as a fork-shaped element 70 having a plurality of prongs 72 extending distally. Each prong 72 engages with one of the distally located loops 20 of the wire frame 12. Of course, any arrangement capable of securing the distal area of the stent to the outer shaft may be used. For example, the distal area of the stent may be secured with retractable pins extending radially outwardly from the outer shaft, wherein the stent is in a secured state with the pins extended and in an unsecured state with the pins retracted. The distal end of the inner shaft 66 includes an atraumatic tip 74 to prevent trauma to the body canal. The atraumatic tip 74 has a distal port 76 and at least one side port 78 for the release of a contrast media or other solutions such as saline, lactated ringer, dextran solution, antibacterial, or angiogenic growth factors. A distal portion of the atraumatic tip 74 is tapered to reduce the likelihood of damaging the tissue of the body canal. The distal area of the stent 10 is lockingly secured to the securing member 68 by having the prongs 72 engage with the loops 20 and abut against the proximal end of the atraumatic tip 74.

The sleeve 62 should be strong enough to withstand the expansion force of the stent 10 but must also be flexible to allow intravascular atraumatic maneuvering. The sleeve 62 may be formed of a high strength thermoplastic elastomer such as nylon, PTFE, polyvinylchloride, PEEK™, ULTEM™ or PEBAX™ or the like. Alternatively, the sleeve 62 may be formed of a braided reinforced polymer tubing or a liner reinforced tubing, preferably having fiber of a polyamide such as VECTRAN™, KEVLAR™, SPECTRA™ or the like embedded to improve tensile strength without reducing flexibility. The outer shaft 64 provides high column strength with flexibility and may be helically formed from a tightly wound, high strength material such as reinforced stainless steel wound over polyimide tubing. The inner shaft 66 may be formed from a polyamide such as ULTEM™, PEEK™, polyvinylchloride, nylon or PTFE, or a thermoset plastic such as polyimide.

To facilitate proper placement of the catheter assembly 52, one or more marker elements 80 may be located at a predetermined position on the sleeve 62, outer shaft 64, and/or inner shaft 66. The marker elements 80 may be a band of metal or radiopaque material attached to the periphery of the sleeve, whereby correct placement of the catheter assembly 52 prior to deployment of the stent 10 may be checked by fluoroscopy. Preferably, the atraumatic tip 74 includes a radiopaque element 82, thereby giving an indication of the location of the distal end of the stent 10 during fluorscopically guided prostheses placement.

Figure 5:
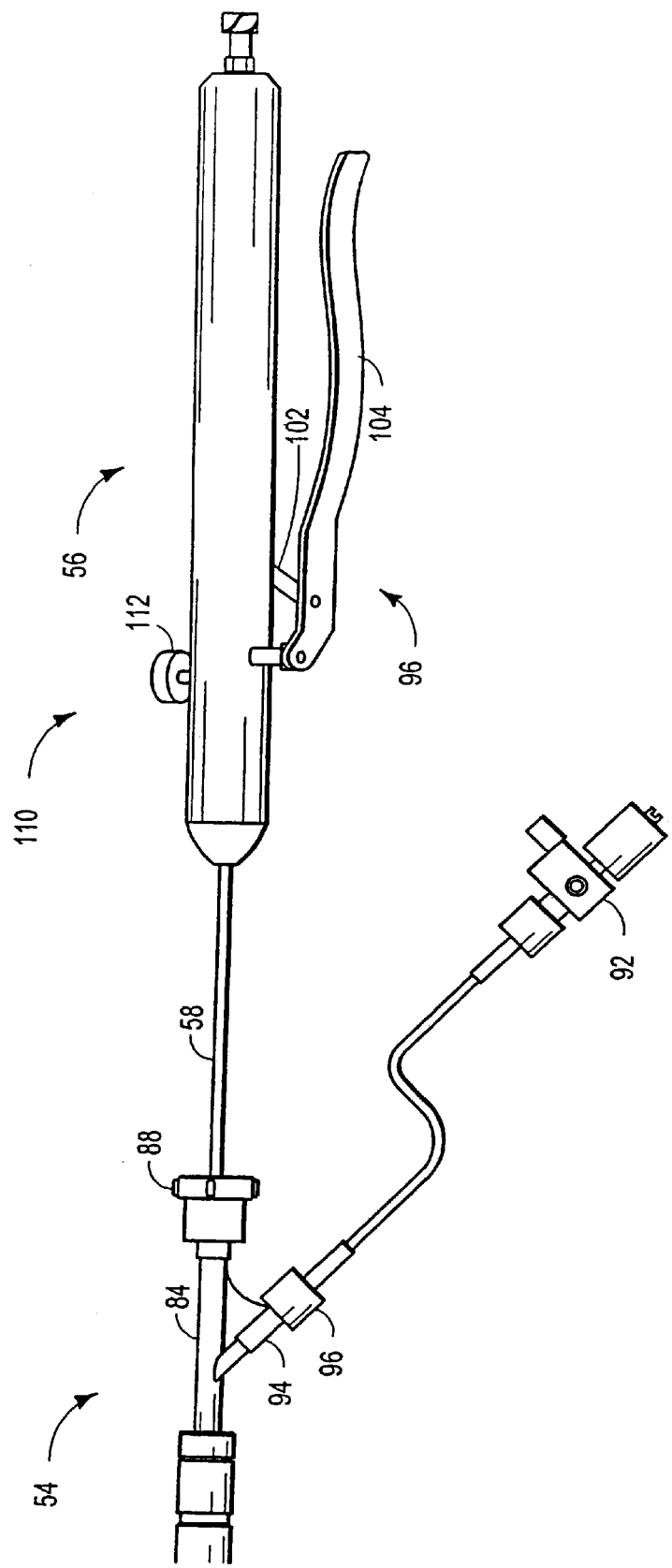
FIG. 5 is a close-up side view of the hand piece and y-connector of the delivery apparatus shown in FIG. 2.

Referring to FIG. 5, the connector 54 comprises a Y-shaped body 84 having mating threaded connector 86 at the proximal end and a compression nut 88 at the distal end. The proximal end of the body 84 is fixedly secured to a distal end of the tube 58 by the mating threaded connector 86. The catheter assembly 52 is disposed within the tube 58 and Y-shaped body and extends outwardly from the compression nut 88. A three-way stop-cock 92 may be connected to an auxiliary port 94 of the body 84 by a luer connector 96. Fluids such as a contrast medium may be introduced into the body canal through the stop-cock 92.

Figure 6:
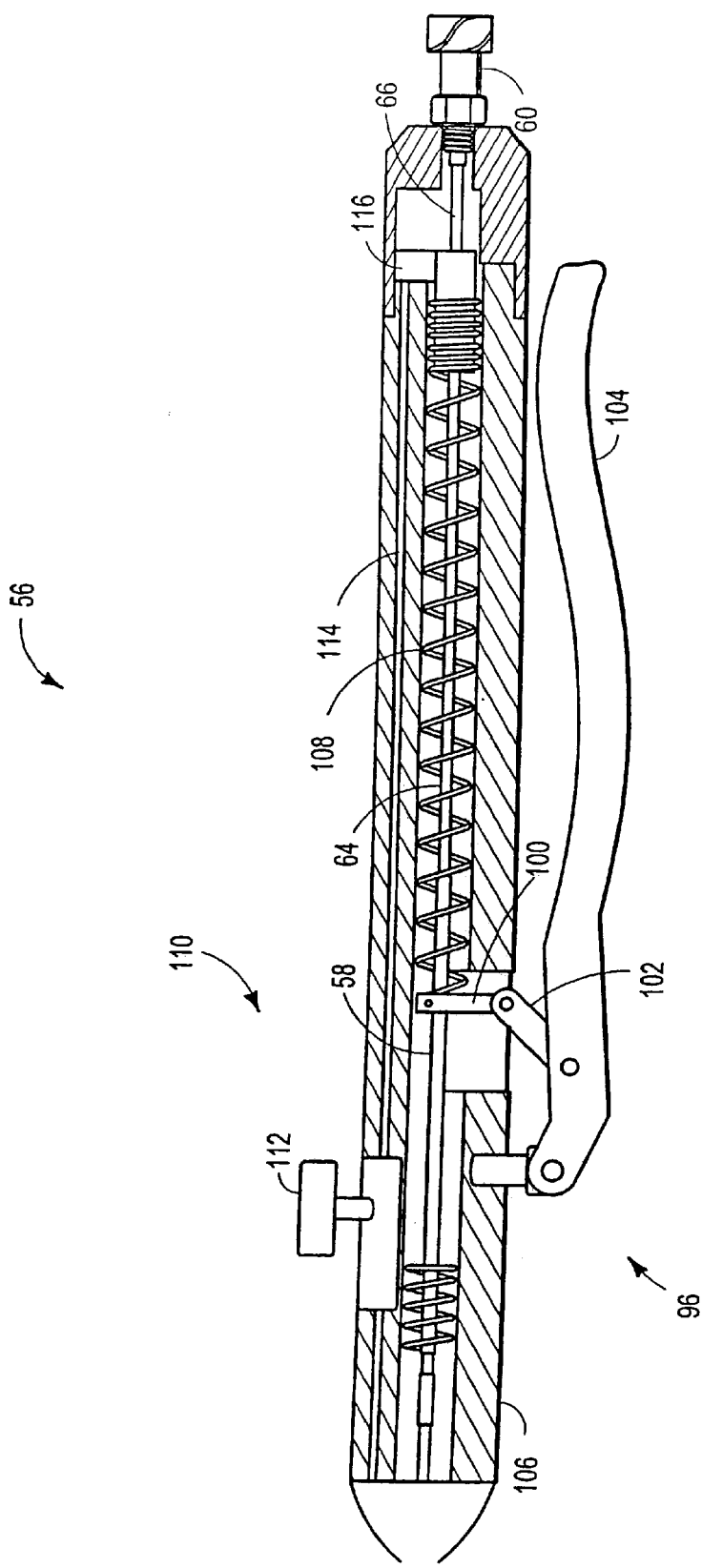
FIG. 6 is a cross-sectional view of the hand piece shown in FIG. 2 with the lever in a retracted position.
Figure 7:
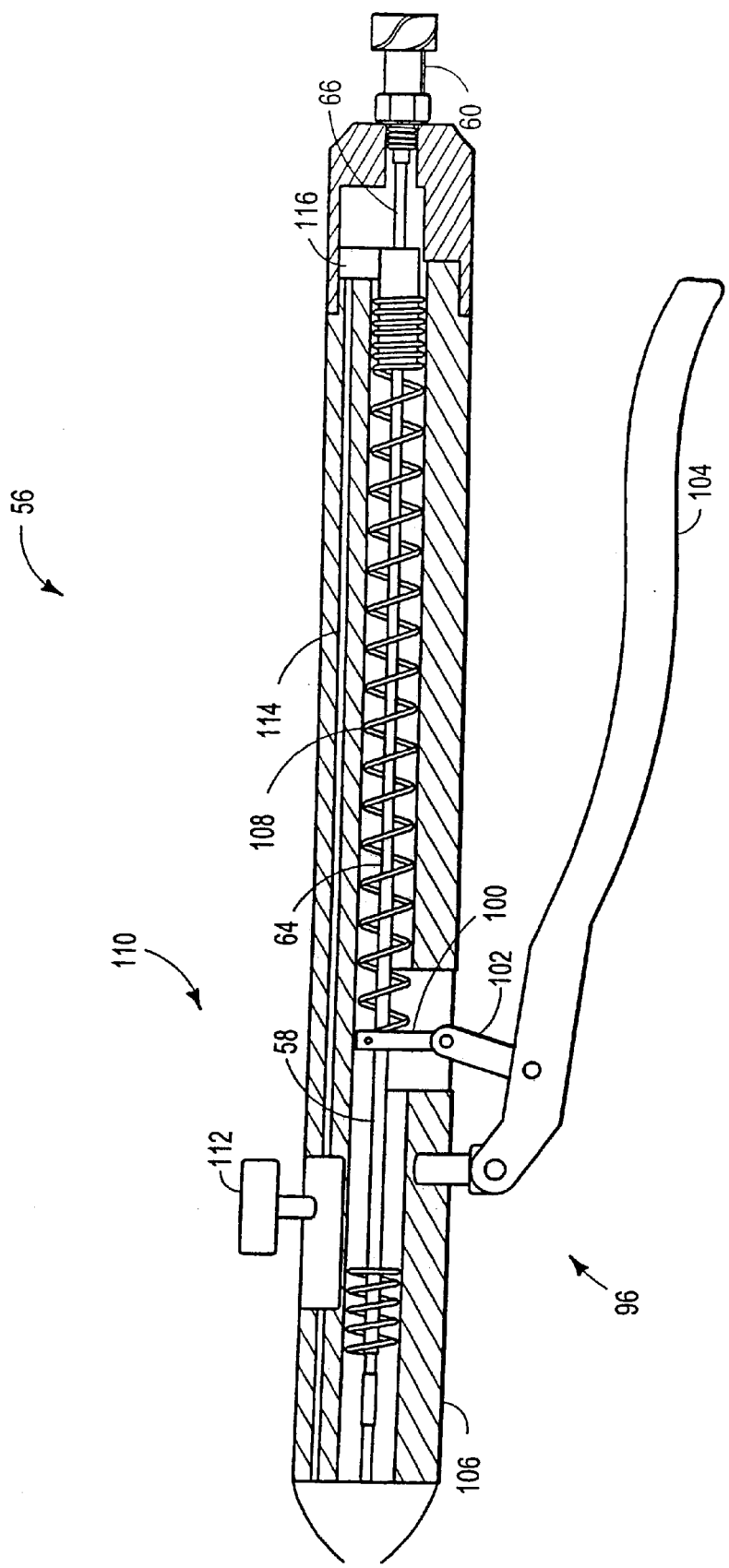
FIG. 7 is a cross-sectional view of the hand piece shown in FIG. 2 with the lever in an extended position.

Referring back to FIG. 5 and FIGS. 6–7, the hand piece 56 is shown. The force required to withdraw the sleeve 62 is substantial, typically in the range of about 5 lbs. For this reason, the hand piece 56 is provided with a lever mechanism 96 to provide a mechanical advantage ratio of about ten to one. The level mechanism 96 is shown in a retracted position in FIG. 6 and in an extended position in FIG. 7. The lever mechanism 96 includes the tube 58, a slider 100, an arm 102, and a lever arm 104. The tube 58 is secured to the sleeve 62 and is slidable relative to the body of the hand piece 56. A first spring 106 is provided to bias the tube 58 towards the distal direction. The slider 100 engages and disengages with the tube 58 to drive the tube 58 in the longitudinal and proximal direction, and a second spring 108 biases the slider 100 towards the distal direction. The lever arm 104 is connected to the slider 100 via the arm 102. Thus, the stent 10 may be incrementally exposed in a precise manner by pressing the lever arm 104, wherein a single stroke drives the tube 58 and sleeve 62 approximately 3 mm in the proximal direction. Depending on the length of the stent 10, full deployment may require the lever arm 104 to be pressed in the range of about 20–30 times.

Referring back to FIGS. 5–7, the hand piece 56 further includes a release mechanism 110 for releasing the stent 10 from the securing member 68. The release mechanism 110 comprises a release knob 112, a rod 114, and a release slider 116. The knob 112 is fixedly connected to the rod 114, the rod 114 is fixedly connected to the release slider 116, and the release slider 116 is fixedly connected to a proximal area of the outer shaft 64. When the release slider 116 is secured to the outer shaft 64, movement of the knob 112 in the proximal direction causes the rod 114, release slider 116, and outer shaft 64 to move in the proximal direction, and the stent 10 is released from the securing member 68.

Clearly, a wide variety of mechanical linkages are available to move the outer sleeve and outer shaft in the distal and proximal directions. It is particularly advantageous to provide a mechanism which allows manipulation with a single hand, thus allowing the alternate hand to manipulate the outer sleeve relative to the hand piece.

Figure 8A:
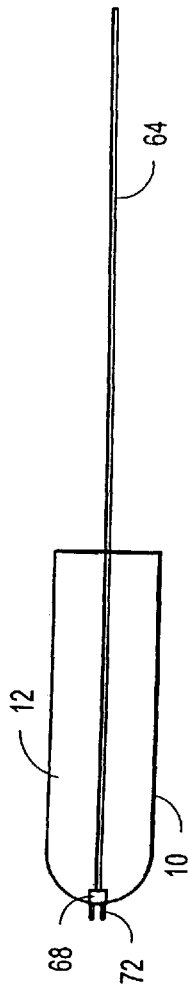
FIGS. 8A–8D illustrate a method of compressing the stent according to the present invention.
Figure 8B:
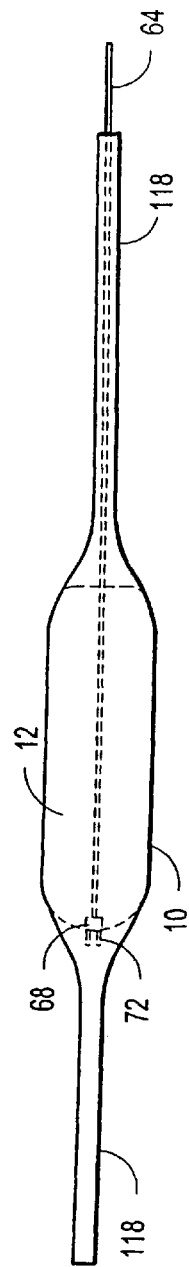

Operation of the delivery apparatus 50 is as follows. Before loading the stent 10 within the sleeve 62, it must be adequately compressed. As shown in FIG. 8A, the outer shaft 64 is secured to the stent 10 by engaging the prongs 72 of the securing member 68 with the loop (not shown) of the wire frame 12. As shown in FIG. 8B, the stent 10 and outer shaft 64 are placed within an expandable, meshed tube 118.

Figure 8C:
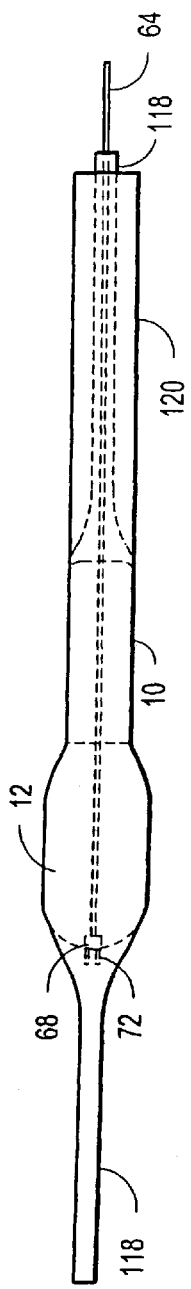
Figure 8D:
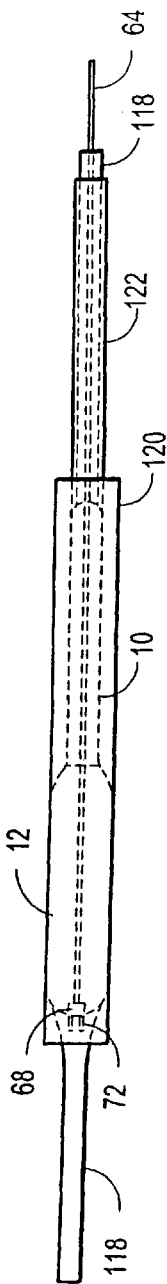

As shown in FIG. 8C, the stent 10, outer shaft 64 and meshed tube 118 are drawn into a first sizing 120 tube having an inner diameter less than the outer diameter of the expanded stent 10, whereby the outer diameter of the stent 10 is reduced to the inner diameter of the sizing tube 120 during the drawing procedure. As shown in FIG. 8D, a portion of a second sizing tube 122, which has an inner diameter less than the inner diameter of the first sizing tube 120, is placed within the first sizing tube 120. The meshed tube 118, stent 10 and outer shaft 64 are drawn into the second sizing tube 122. Additional sizing tubes with incrementally smaller inner diameters may be used to further compress the stent 10.

Figure 9A:
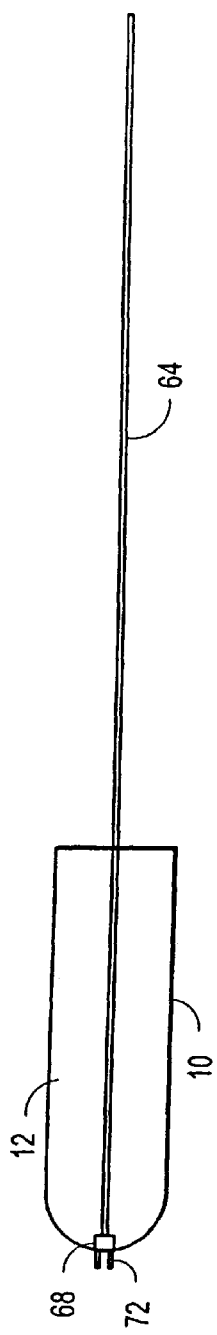
FIGS. 9A–9C illustrate another method of compressing the stent according to the present invention.
Figure 9B:
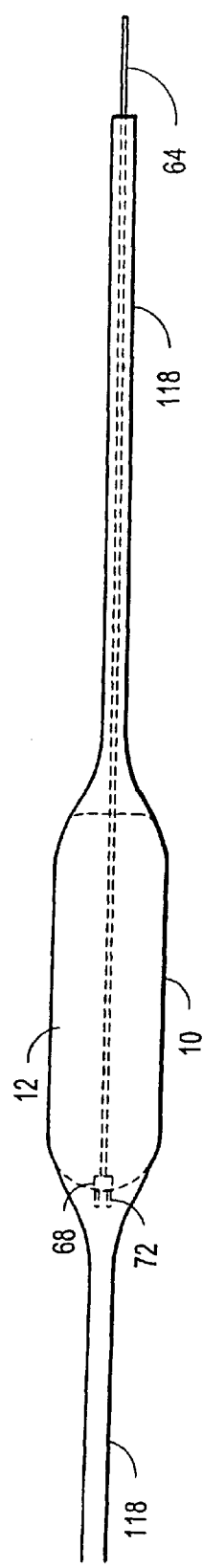
Figure 9C:
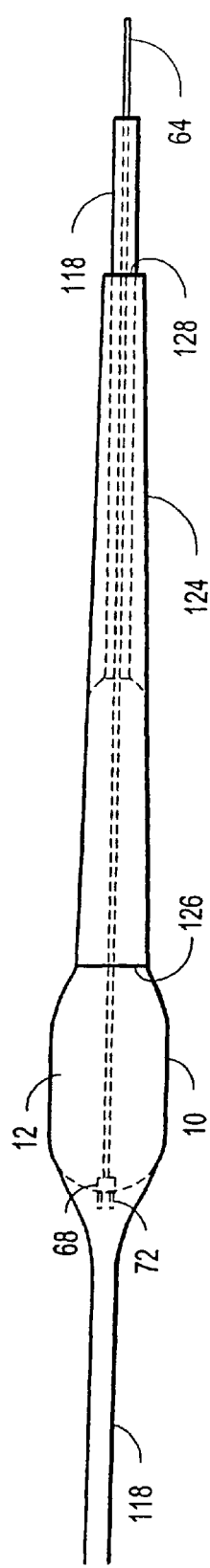

An alternative method to compress the fully expanded stent 10 is shown in FIGS. 9A–9C. As shown in FIG. 9A, the outer shaft 64 is secured to the stent 10 by engaging the prongs 72 of the securing member 68 with the loops (not shown) of the wire frame 12. As shown in FIG. 9B, the stent 10 and outer shaft 64 are placed within the expandable, meshed tube 118. As shown in FIG. 9C, the meshed tube 118, stent 10 and outer shaft 64 are drawn into a conically shaped sizing tube 124, wherein the inner diameter of a load end 126 is larger that an exit end 128. It is noted that other means may be utilized to compress the stent such as by using pull wires run through the stent loops, or by crimping, folding, or wrapping.

Figure 10A:
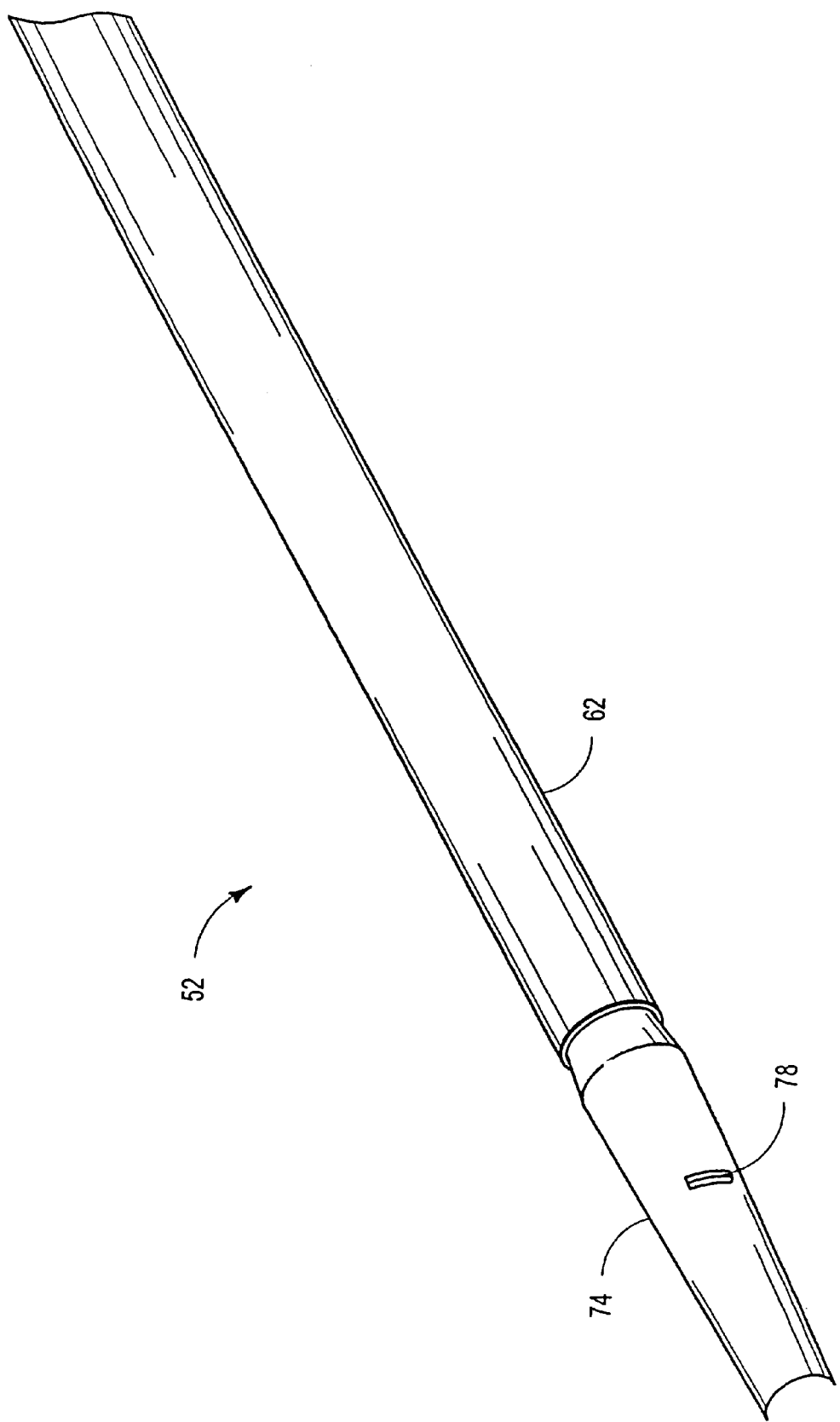
FIGS. 10A–10F illustrate various stages in the deployment of the stent shown in FIG. 1.

To prepare the catheter assembly 52, the compressed stent 10 is transferred from the sizing tube 122 or 124 to the distal area of the sleeve 62 by sliding the outer shaft 64 into the lumen of the sleeve 62. The meshed tube 118 is removed from the outer shaft 64. Via the distal end of the outer shaft 64, the inner shaft 66 is passed through the outer shaft 64 until the atraumatic tip 74 abuts against the securing member 68. FIG. 10A illustrates the distal area of the catheter assembly 52 when in a pre-deployment stage.

Assuming an introducer (not shown) has been inserted into the body canal, a guide wire (not shown) may be positioned at the occlusion site. The catheter assembly 52 is passed over the guide wire via the lumen of the inner shaft 66 and directed to the occlusion site. With the catheter assembly 52 properly positioned within the body canal. The guide wire may be retained within the inner shaft 66 until the stent 10 is deployed at the desired location and withdrawn together with the catheter assembly. Alternatively, the guide wire may be withdrawn prior to deployment of the stent 10 so that correct positioning of the stent 10, while still within the catheter assembly 52, may be verified by endoscopic or fluoroscopic means or the like.

Figure 10B:
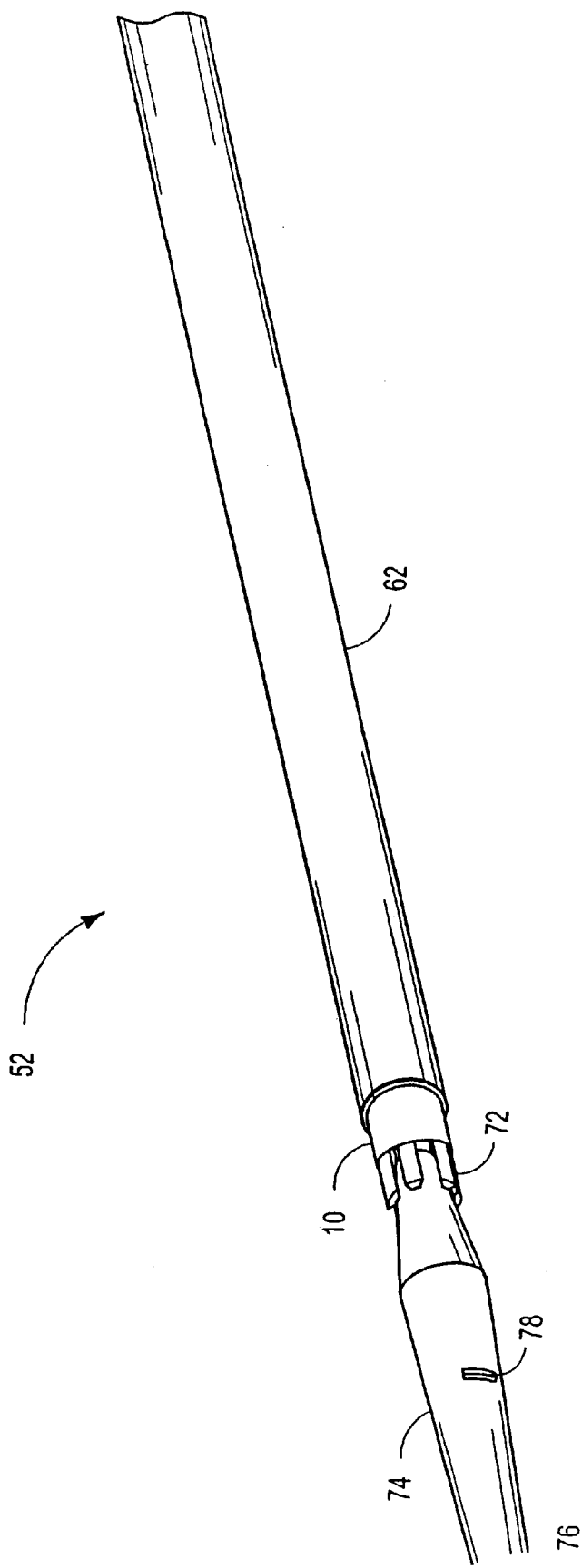
Figure 10C:
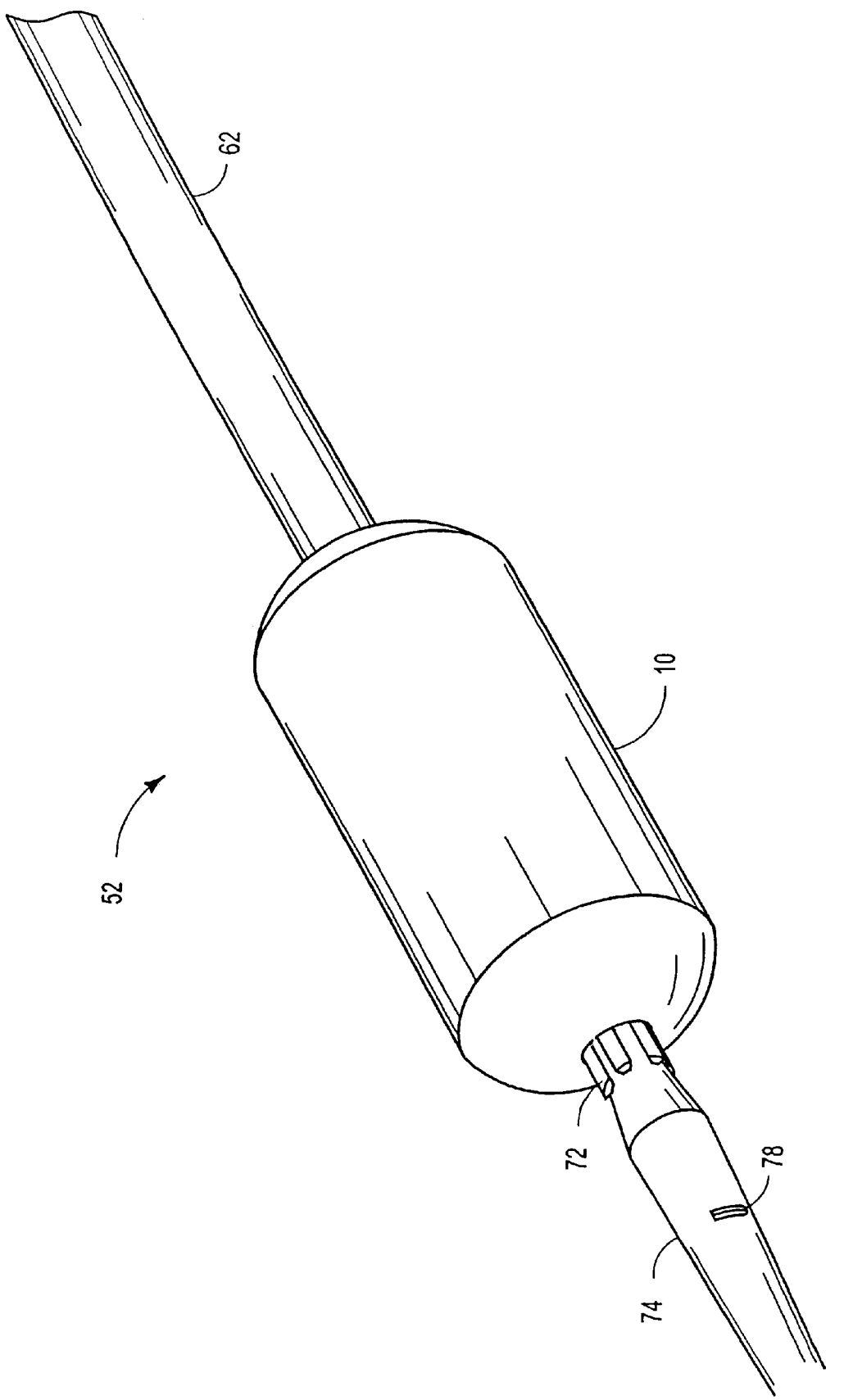
Figure 10D:
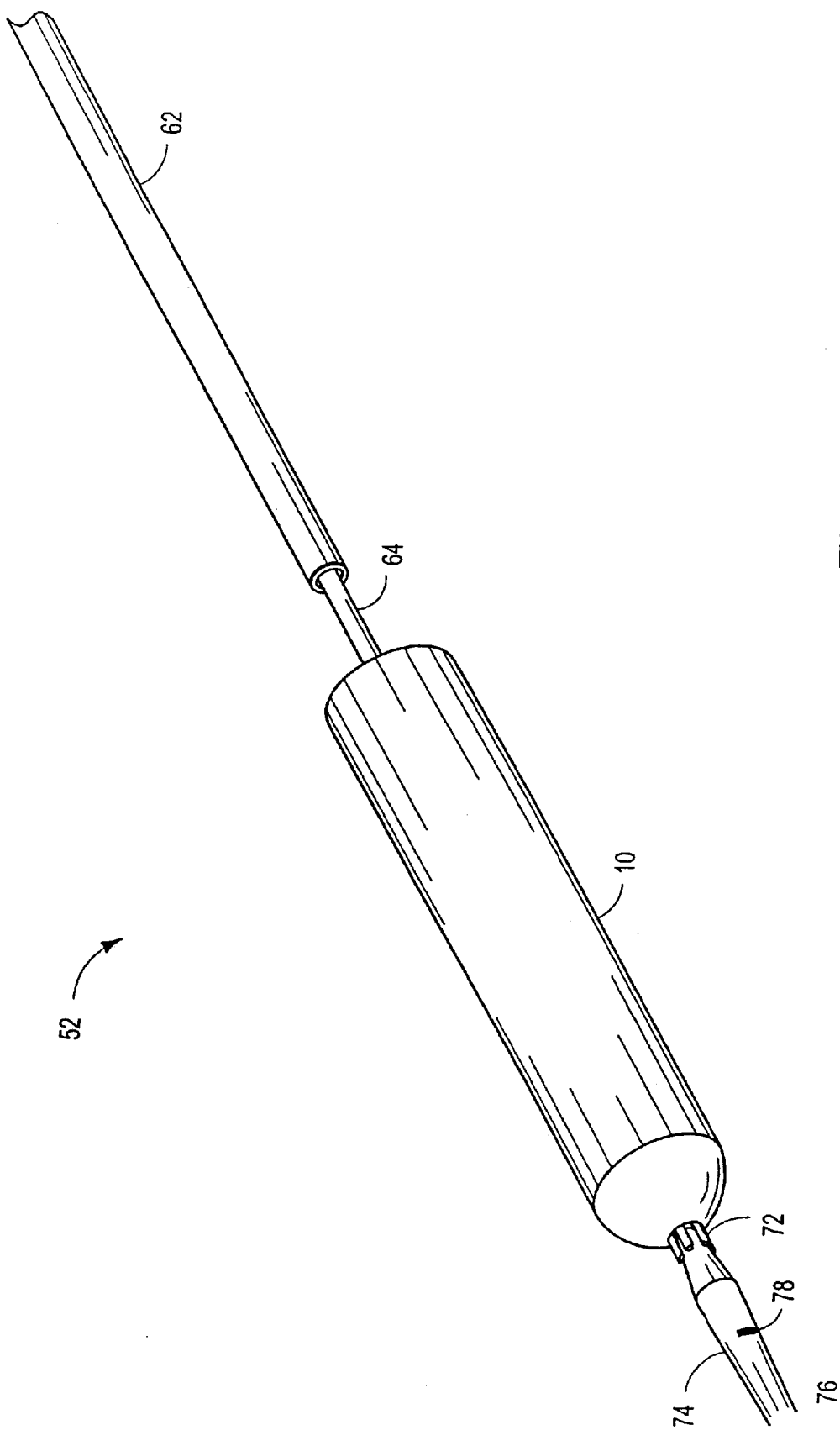
Figure 10E:
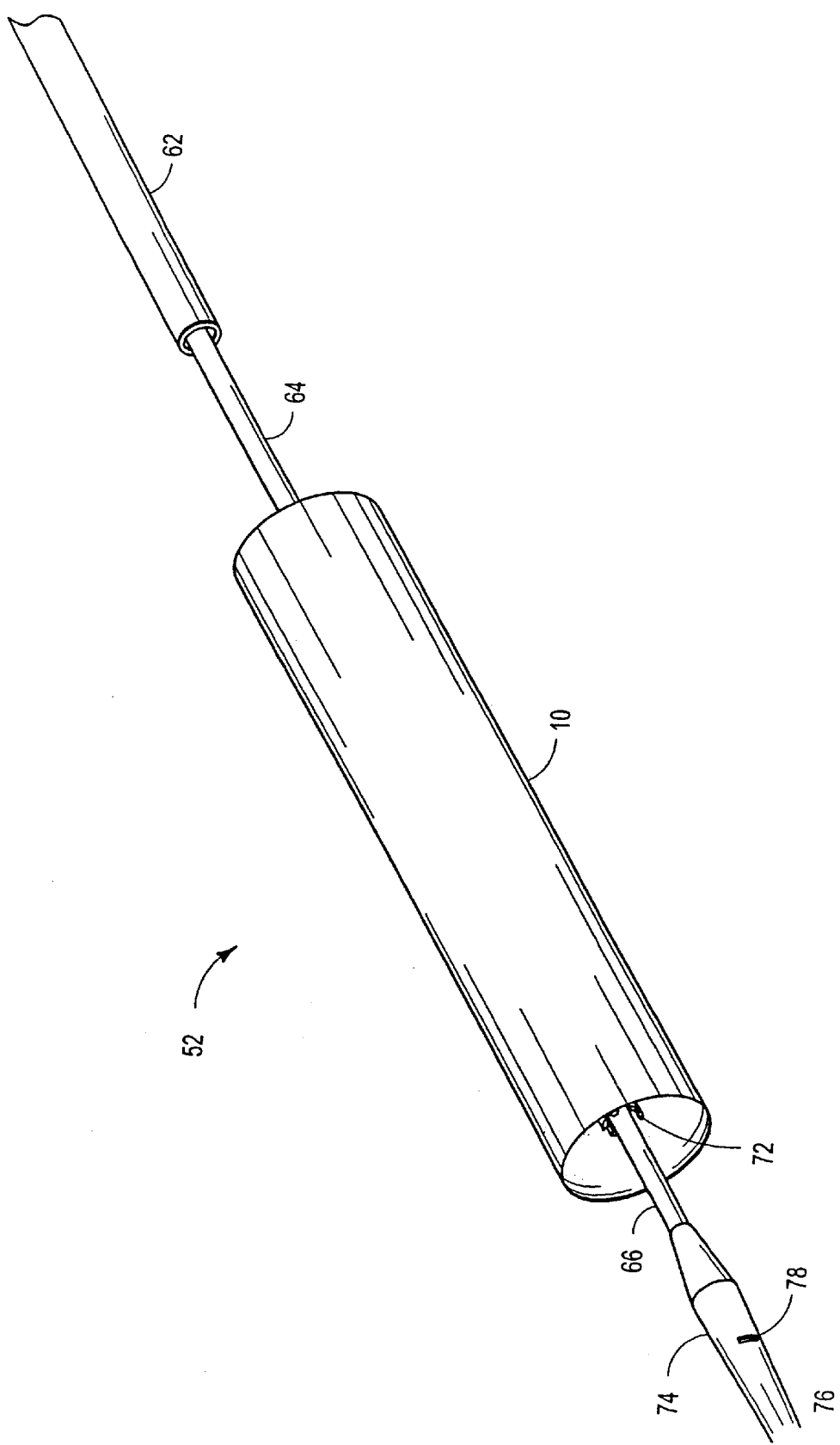
Figure 10F:
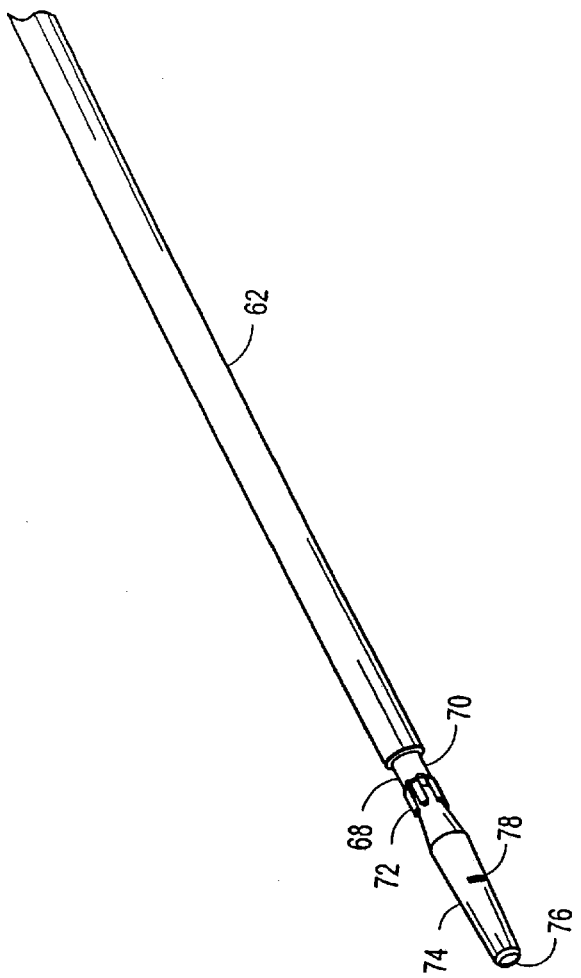
Figure 10F:
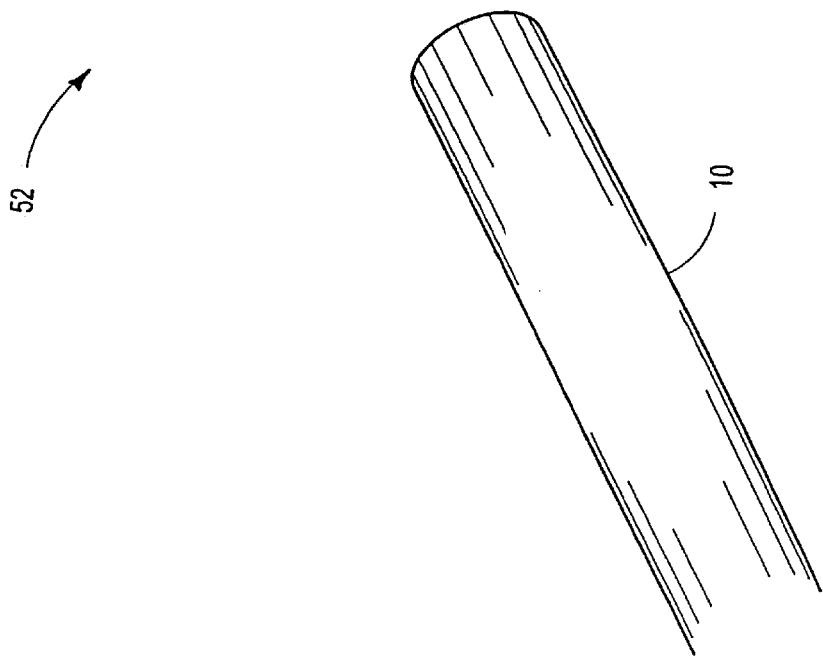

The positioning of the catheter assembly 52 within the body canal may be monitored and verified by locating the one or more marker elements 80 by use of an endoscope or by fluoroscopy. When the correct position for proper placement of the stent 10 is reached and verified, the stent 10 is then deployed by retracting the sleeve 62 relative to the outer shaft 64 and by retracting the outer shaft relative to the inner shaft 66. The operation is performed by gripping the hand piece 56 and repeatedly pressing the lever arm 104 to incrementally retract the sleeve 62 in the longitudinal and proximal direction, thus exposing the stent 10. FIGS. 10B and 10C illustrate the stent 10 in a partially exposed state. At this stage, the exposed portion of the stent 10, with the exception of the distal area, is free to partially expand. Before the stent 10 is completely exposed, the positioning of the stent 10 within the body canal is rechecked. If the position is correct, retraction of the sleeve 62 is continued until the stent 10 is clear of the sleeve 62 as shown in FIG. 10D. To release the stent 10 from the outer shaft 64, the release member knob 112 is actuated, and the inner shaft 66 and securing member 68 are retracted in the longitudinal and proximal direction. The stent 10 is released from the securing member 68 as shown in FIG. 10E, and the catheter assembly 52 is then withdrawn from the stent 10 as shown in FIG. 10F. However, if the monitoring reveals that the stent 10 is not in its proper position, further retraction of the sleeve 62 is terminated. Since the securing member 68 prevents the stent from being fully expanded, the catheter assembly 52 may be repositioned as required, and the deployment operation can be completed with the stent 10 in its correct position. As discussed above, one of the advantages of the present invention is that repositioning of the catheter assembly 52 does not require the step of fully compressing the stent 10 by distally driving the sleeve 62 to fully enclose the stent 10. Furthermore, when deploying a stent with high compressibility, the column strength of the stent actually aids in repositioning.

Although the present invention has been described in detail with regarding the exemplary embodiment and drawings thereof, it should be apparent to those skilled in the art that various adaptations may be accomplished without departing from the spirit and scope of the invention. For example, the catheter assembly may comprise only two elongated members. The first elongated member may contain the stent, while the second elongated member has a clamping mechanism at its distal area which does not require an inner shaft to lockingly secure the stent, For example, the clamping mechanism may have retractable pins which lockingly secure the stent. During deployment of the stent, the pins may be retracted from the second elongated member. Further, other means may be utilized to drive the sleeve, outer shaft, and inner shaft. For example, the sleeve may have a first handle at its proximal end, and the outer shaft may have a second handle at its proximal end. The sleeve may be retracted by holding the first handle and pulling it in the proximal direction, thus exposing the stent. The stent may be released from the securing member by holding the second handle and pulling it in the proximal direction. In another example, the sleeve and outer shaft may be contained within rotatable transfer assemblies similar to a fly, fishing reel. Accordingly, the invention is not limited to the precise embodiment shown in the drawings and described in detail hereinabove.

What is claimed is:

1. A method for deploying a prosthesis within a body canal, the method comprising:

providing an outer shaft having a distal area, the distal area having a securing member;

securing a distal area of the prosthesis onto the outer shaft with the securing member;

providing a sleeve having a distal area;

containing the prosthesis within the distal area of the sleeve and positioning the outer shaft within the sleeve;

the process further comprising the steps of:

positioning the prosthesis within the body canal at a desired location; and deploying the prosthesis at the desired location by causing longitudinal motion between the sleeve and the outer shaft to expose the prosthesis, keeping the distal area of the prosthesis engaged with the securing member while permitting the exposed portion of the prosthesis to be free to partially expand;

wherein the step of providing a hand piece includes having a lever arm coupled to the sleeve;

actuating the lever arm to incrementally and precisely drive the sleeve in a longitudinal and proximal direction such that the sleeve moves in a proximal direction relative to the outer shaft;

fully exposing the prosthesis while maintaining securement to the outer shaft by the securing member; and releasing the prosthesis from the outer shaft by disengaging the securing member;

while re-positioning the prosthesis within the body canal at a desired location;

fully exposing the prosthesis while maintaining securement to the outer shaft by the securing member; and releasing the prosthesis from the outer shaft by disengaging the securing member; the method likewise including the steps of:

providing an inner shaft having a distal area, the distal area having a tip;

positioning the inner shaft within the outer shaft in a slidable manner;

wherein the securing member is a fork-shaped element having at least one prong which engages with the distal area of the prosthesis;

lockingly securing the prosthesis onto the securing member by slidingly coupling the inner shaft with the outer shaft so that a distal end of the at least one prong abuts against a proximal end of the tip; and releasing the prosthesis from the securing member by longitudinally and proximally sliding the inner shaft relative to the outer shaft so that the securing member is slidingly displaced away from the tip.

2. A method for deploying a prosthesis within a body canal, the method comprising:

providing an outer shaft having a distal area, the distal area having a securing member;

securing a distal area of the prosthesis onto the outer shaft with the securing member;

providing a sleeve having a distal area;

containing the prosthesis with the distal area of the sleeve and positioning the outer shaft within the sleeve;

the process further comprising the steps of:

positioning the prosthesis within the body canal at a desired location; and deploying the prosthesis at the desired location by causing longitudinal motion between the sleeve and the outer shaft to expose the prosthesis, keeping the distal area of the prosthesis engaged with the securing member while permitting the exposed portion of the prosthesis to be free to partially expand;

wherein the step of providing a hand piece includes having a lever arm coupled to the sleeve;

actuating the lever arm to incrementally and precisely drive the sleeve in a longitudinal and proximal direction such that the sleeve moves in a proximal direction relative to the outer shaft;

fully exposing the prosthesis while maintaining securement to the outer shaft by the securing member; and releasing the prosthesis from the outer shaft by disengaging the securing member;

while re-positioning the prosthesis within the body canal at a desired location;

fully exposing the prosthesis while maintaining securement to the outer shaft by the securing member; and releasing the prosthesis from the outer shaft by disengaging the securing member; the method likewise including the steps of:

providing an inner shaft having a distal area, the distal area having a tip;

positioning the inner shaft within the outer shaft in a slidable manner;

wherein the securing member is a fork-shaped element having at least one prong which engages with the distal area of the prosthesis;

lockingly securing the prosthesis onto the securing member by slidingly coupling the inner shaft with the outer shaft so that a distal end of the at least one prong abuts against a proximal end of the tip; and releasing the prosthesis from the securing member by longitudinally and proximally sliding the inner shaft relative to the outer shaft so that the securing member is slidingly displaced away from the tip;

whereby, the process comprises the step of providing the tip with a side port for the release of a contrast medium into the body canal, whereby the contrast agent is released near the prosthesis, and whereby said tip is an atraumatic tip for reducing injury to the body canal.

3. A method for deploying a prosthesis within a body canal, the method comprising:

providing an outer shaft having a distal area, the distal area having a securing member;

securing a distal area of the prosthesis onto the outer shaft with the securing member;

providing a sleeve having a distal area;

containing the prosthesis within the distal area of the sleeve and positioning the outer shaft within the sleeve;

the process further comprising the steps of:

positioning the prosthesis within the body canal at a desired location; and deploying the prosthesis at the desired location by causing longitudinal motion between the sleeve and the outer shaft to expose the prosthesis, keeping the distal area of the prosthesis engaged with the securing member while permitting the exposed portion of the prosthesis to be free to partially expand;

wherein the step of providing a hand piece includes having a lever arm coupled to the sleeve;

actuating the lever arm to incrementally and precisely drive the sleeve in a longitudinal and proximal direction such that the sleeve moves in a proximal direction relative to the outer shaft;

fully exposing the prosthesis while maintaining securement to the outer shaft by the securing member; and releasing the prosthesis from the outer shaft by disengaging the securing member;

while re-positioning the prosthesis within the body canal at a desired location;

fully exposing the prosthesis while maintaining securement to the outer shaft by the securing member; and releasing the prosthesis from the outer shaft by disengaging the securing member; the method likewise including the steps of:

providing an inner shaft having a distal area, the distal area having a tip;

positioning the inner shaft within the outer shaft in a slidable manner;

wherein the securing member is a fork-shaped element having at least one prong which engages with the distal area of the prosthesis;

lockingly securing the prosthesis onto the securing member by slidingly coupling the inner shaft with the outer shaft so that a distal end of the at least one prong abuts against a proximal end of the tip; and releasing the prosthesis from the securing member by longitudinally and proximally sliding the inner shaft relative to the outer shaft so that the securing member is slidingly displaced away from the tip;

wherein the hand piece further comprises a tube connecting the sleeve to the lever arm, so that actuating the lever drives the tube in a proximal direction and movement of the tube causes the sleeve to be driven in a proximal direction.

4. A method for deploying a prosthesis within a body canal, the method comprising:

providing an outer shaft having a distal area, the distal area having a securing member;

securing a distal area of the prosthesis onto the outer shaft with the securing member;

providing a sleeve having a distal area;

containing the prosthesis within the distal area of the sleeve and positioning the outer shaft within the sleeve;

the process further comprising the steps of:

positioning the prosthesis within the body canal at a desired location; and deploying the prosthesis at the desired location by causing longitudinal motion between the sleeve and the outer shaft to expose the prosthesis, keeping the distal area of the prosthesis engaged with the securing member while permitting the exposed portion of the prosthesis to be free to partially expand;

wherein the step of providing a hand piece includes having a lever arm coupled to the sleeve;

actuating the lever arm to incrementally and precisely drive the sleeve in a longitudinal and proximal direction such that the sleeve moves in a proximal direction relative to the outer shaft;

fully exposing the prosthesis while maintaining securement to the outer shaft by the securing member; and releasing the prosthesis from the outer shaft by disengaging the securing member;

while re-positioning the prosthesis within the body canal at a desired location;

fully exposing the prosthesis while maintaining securement to the outer shaft by the securing member; and releasing the prosthesis from the outer shaft by disengaging the securing member; the method likewise including the steps of:

providing an inner shaft having a distal area, the distal area having a tip;

positioning the inner shaft within the outer shaft in a slidable manner;

wherein the securing member is a fork-shaped element having at least one prong which engages with the distal area of the prosthesis;

lockingly securing the prosthesis onto the securing member by slidingly coupling the inner shaft with the outer shaft so that a distal end of the at least one prong abuts against a proximal end of the tip; and releasing the prosthesis from the securing member by longitudinally and proximally sliding the inner shaft relative to the outer shaft so that the securing member is slidingly displaced away from the tip;

biasing the tube in a distal direction with a spring, and, additionally including the step of:

providing the hand piece with a release member to drive the outer shaft in a proximal direction relative to the inner shaft; and actuating the release member to release the securing member from the prosthesis.

* * * * *